United States Patent [19]

Bowman et al.

[11] Patent Number: 4,985,206

[45] Date of Patent: Jan. 15, 1991

[54] TISSUE PROCESSING APPARATUS

[75] Inventors: David J. Bowman, Manchester; Raymond F. Cosgrove, Wallasey; Terence P. Male, Helsby; Robert Evans, Liverpool, all of England

[73] Assignee: Shandon Scientific Limited, Runcorn, England

[21] Appl. No.: 250,929

[22] Filed: Sep. 29, 1988

[30] Foreign Application Priority Data

Sep. 30, 1987 [GB] United Kingdom ............... 8722902

[51] Int. Cl.⁵ .................... B01L 11/00; B05C 21/00; G01N 21/00
[52] U.S. Cl. .................... 422/99; 422/102; 422/104; 422/58; 435/292; 435/299; 350/536; 356/244; 118/500
[58] Field of Search .................... 422/55, 57, 58, 63, 422/64, 99–102, 104; 435/285, 292, 299; 356/244, 246; 350/534, 536; 118/401, 500, 501; 427/2, 4

[56] References Cited

U.S. PATENT DOCUMENTS

| | | | |
|---|---|---|---|
| 4,245,907 | 1/1981 | Rosen | 350/536 |
| 4,501,496 | 2/1985 | Griffin | 356/246 |
| 4,629,703 | 12/1986 | Uffenheimer | 422/64 |
| 4,731,335 | 3/1988 | Brigati | 422/100 |
| 4,790,640 | 12/1988 | Nason | 350/536 |
| 4,883,760 | 11/1989 | Heelies | 435/287 |

FOREIGN PATENT DOCUMENTS 0113732 7/1983 Japan ................... 422/102

Primary Examiner—Robert A. Wax
Assistant Examiner—William H. Beisner
Attorney, Agent, or Firm—Vaden, Eickenroht, Thompson & Boulware

[57] ABSTRACT

A tissue or like processing method involving application of liquids to carrier-mounted material, e.g. a thin tissue section mounted on a microscope slide (10), is characterized by disposing a channel-defining element (1) adjacent to the carrier (10) to form an assembly providing an enclosure (11) for the material on the carrier. The enclosure (11) has an inlet (13) and an outlet (14) and has capillary dimensions. The assembly is disposed with the inlet (13) above the outlet (14) and liquid introduced into the inlet fills the enclosure and is retained in contact with the material on the carrier by surface tension effect. Further liquid introduced to the inlet (13) displaces the first liquid progressively to the outlet (14). A sequence of liquids can thus be brought successively into contact with the material with minimum wastage, by feeding the liquids successively to the inlet (13) of an assembly. A support for a plurality of assemblies to permit concurrent operations upon a set of material samples is disclosed, and a machine for automated processing, e.g. immunostaining, of a batch of tissue samples is also disclosed.

4 Claims, 5 Drawing Sheets

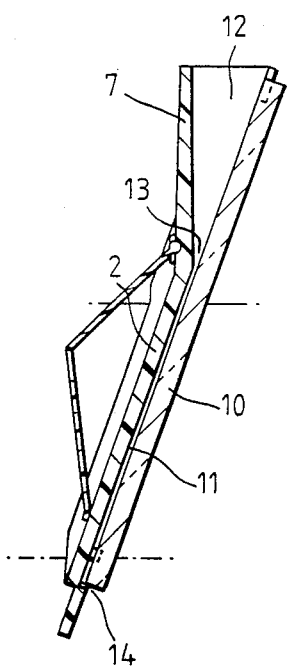
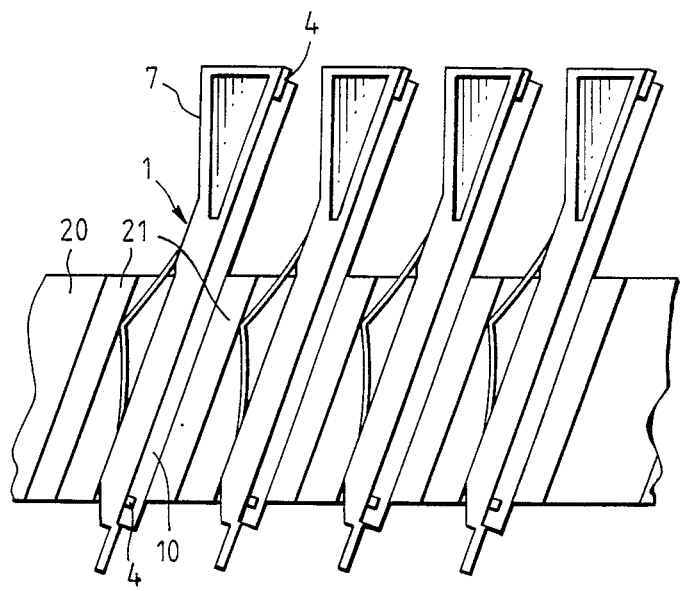
*Fig.10.*
*Fig.11.*
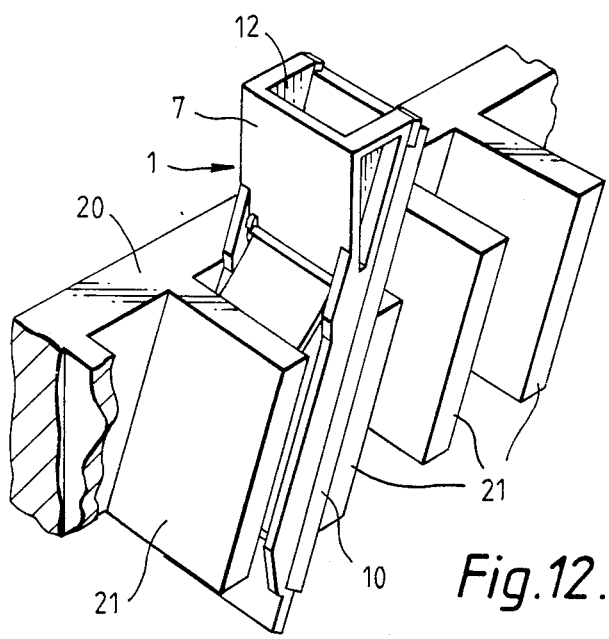
*Fig.12.*

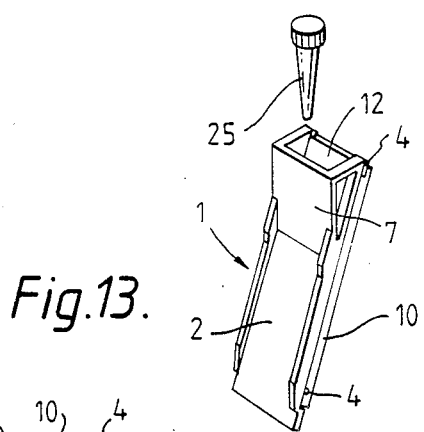
Fig.13.
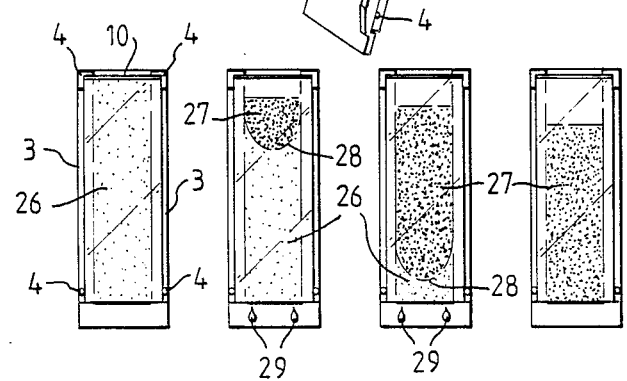
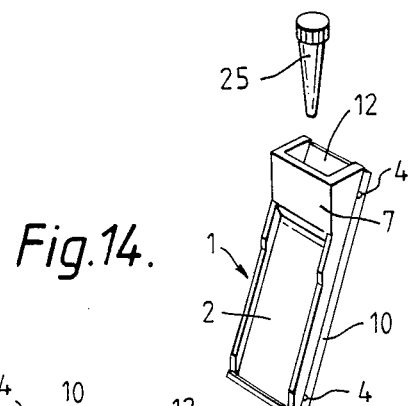
Fig.14.
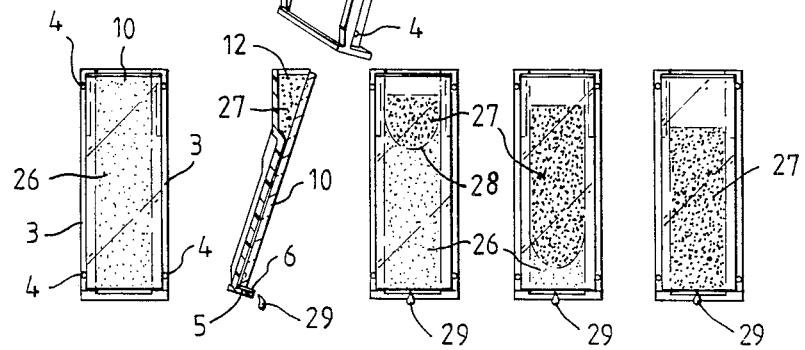

TISSUE PROCESSING APPARATUS

This invention relates to the processing of tissue and like material for, e.g., histological and cytological examination purposes. The invention is especially concerned with the processing of tissue and like material in the form of thin sections or deposits on a slide or similar carrier.

BACKGROUND AND FIELD OF THE INVENTION

In typical histological practice, a bulk tissue specimen is processed by treatment with a succession of fluids or vapours to extract its aqueous content so as to allow of its impregnation with wax or resin to provide the specimen with sufficient rigidity to enable thin sections to be cut from it with a microtome. Sections of interest are then mounted on slides or other carriers and, usually, further processed thereon so that they display required characteristics for microscopic examination. For instance, a mounted tissue section may be processed to remove the wax or resin and to accomplish rehydration so that the tissue section is receptive to dyes or other staining agents.

The processing of bulk tissue specimens has been largely automated in modern laboratory practice. Similarly, significant automation of the processing of slide-mounted tissue sections has been achieved in practice. However, whereas the liquids and other reagents used for processing bulk tissue specimens are relatively inexpensive so that processing techniques involving their use in large quantities are acceptable in practice, some of the processing techniques now being applied to slide mounted materials involve the use of reagents that are costly and require to be applied to the material in very small quantities under closely controlled conditions of temperature and duration. The so called "immuno-staining" procedures are cases in point. Existing techniques lack the controllability and/or economy of reagents desirable for such procedures.

SUMMARY OF THE INVENTION

An object of the present invention is to provide for the controlled application of small quantities of fluids sequentially to a tissue or like material on a slide or like carrier, and especially to facilitate the automation of procedures such as immuno-staining.

In accordance with one aspect of the invention, a method of applying liquids to a carrier-mounted material is characterised by disposing a channel-defining element adjacent to the carrier to form an assembly providing an enclosure for the material on the carrier, said enclosure having an inlet and an opposed outlet and being internally shaped to provide a clearance of capillary dimensions over the carrier and, with the assembly disposed so that said inlet is above said outlet, introducing liquid into the inlet to be retained in contact with the said material by surface tension effect, and subsequently displacing said liquid to said outlet by introducing another liquid into said inlet.

By "capillary dimensions" we mean dimensions sufficiently small for surface tension effects to be effective to hold a liquid in contact with the material when the assembly is disposed with the material-bearing surface of the carrier in a vertical or near vertical attitude. Clearances of the order of 50 um have this characteristic.

It has been found that by this method, extremely small quantities of liquid can be spread over and held in contact with material on the surface of a slide or like carrier, and can then be displaced with negligible mixing by a subsequently introduced liquid. The method thus enables a succession of very small quantities of, e.g., staining reagents to be brought sequentially into contact with, for instance, a tissue section with negligible mixing of the individual reagents during the displacement of one by the next.

In preferred practice of the method, the assembly of channel-defining element and carrier are preferably supported in a near vertical attitude: that is to say, with the surface of the slide or like carrier disposed in a near vertical plane, for instance at an angle of about 70° to the horizontal.

Provision may be made for controlling the temperature of at least the carrier of the assembly.

The invention also provides apparatus for performing the foregoing method. Thus in another aspect the invention provides an enclosure member including a channel-defining element adapted to overlap and be secured to a material carrier to define therewith a passage of capillary dimensions having an inlet and an opposed outlet.

Preferably the enclosure member further includes a funnel-defining element communicating with the inlet to said passage to facilitate the introduction of liquids to the passage via the inlet. The funnel-defining element may conveniently be configured to define a funnel in conjunction with a material carrier when that is assembled with the member.

The enclosure member may also include a sump that communicates with the outlet of said passage.

The apparatus may further comprise a support for one or more of said assemblies. In preferred embodiments the support comprises a generally horizontal rail having pairs of laterally extending parallel fins to receive therebetween an aforesaid assembly and to hold the same in a near vertical attitude.

The fins of such a support may be equipped for supplying heat to or abstracting heat from the material carriers of assemblies located between such fins. For instance, the fins may be associated with heating coils and/or have coolant fluid passages.

BRIEF DESCRIPTION OF THE DRAWINGS

FIG. 10 is a sectional illustration of a slide clip assembled with a microscope slide as a material carrier;

FIG. 11 is a side elevational view of a plurality of assemblies as shown in FIG. 10 mounted in a section of a support member;

FIG. 12 is a pictorial view of a single assembly carried by the support member;

FIG. 13 illustrates pictorially the operation of the assembly of FIG. 10, when the slide clip is of the form shown in FIGS. 1 to 5;

FIG. 14 corresponds with FIG. 13 but illustrates operation with a slide clip of the form shown in FIGS. 6 to 9.

DETAILED DESCRIPTION OF PREFERRED EMBODIMENTS

Figure 1:
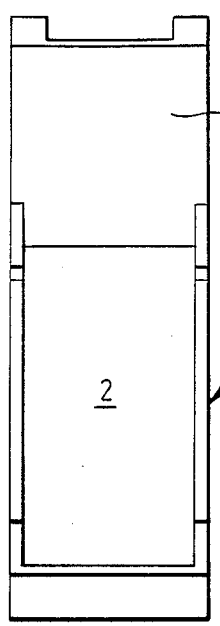
FIGS. 1 to 5 are elevation and sectional views of one form of slide clip embodying the invention.

FIGS. 1 to 5 of the drawings illustrate an embodiment of a slide clip intended for association with a material carrier in the form of a standard glass microscope slide and for use with a support of the form to be described in connection with FIGS. 11 and 12. These Figures show a slide clip generally referenced 1 that is conveniently a moulding of suitable plastics material and comprises a channel defining element constituted by a web 2 and flanges 3 that project approximately 70 um from the face of the web 2. The overall width of the channel-defining element across the flanges 3 corresponds with the width of a standard glass microscope slide. The outer aspects of the flanges 3 carry a pair each of lugs and pegs 4 for locating against the edges of a microscope slide when that is assembled with the clip 1.

In the alternative form of slide clip illustrated in FIGS. 6 to 9, there are two pairs of locating pegs 4 and the lower end of the clip has a lug 5 with shoulders 6 for cooperation with the lower end of a slide to define a sump for discharging liquid as hereinafter explained. Otherwise the slide clip of FIGS. 6 to 9 corresponds in configuration with that of FIGS. 1 to 5 and corresponding parts have the same references.

Figure 2:
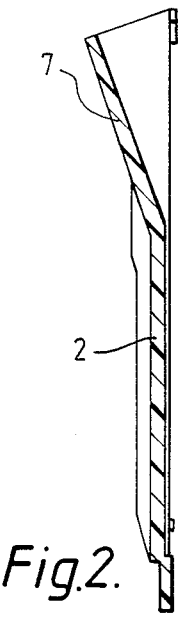
Figure 3:
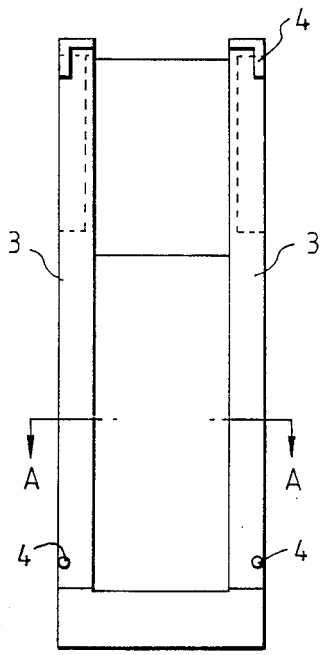
Figure 4:
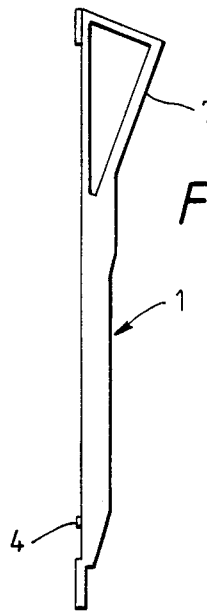
Figure 5:
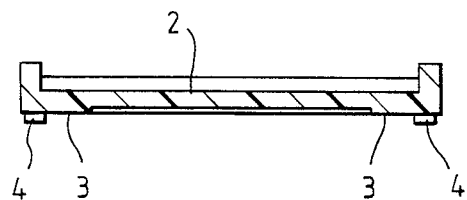
Figure 6:
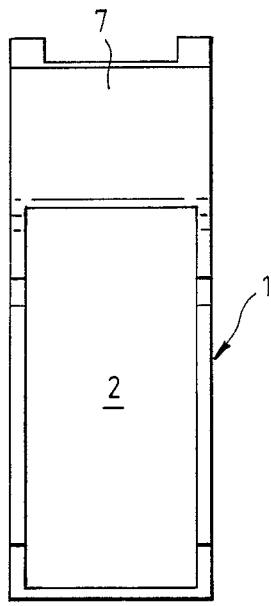
FIGS. 6 to 9 are elevation and sectional views of another form of the slide clip, incorporating a sump.
Figure 7:
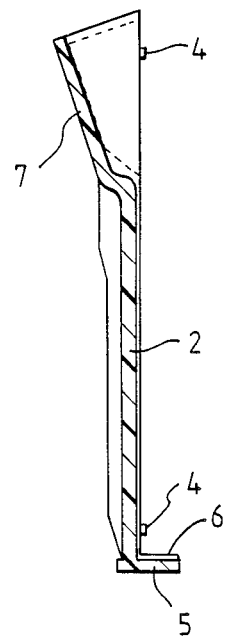
Figure 8:
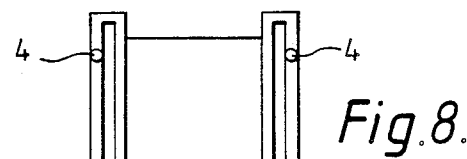
Figure 9:
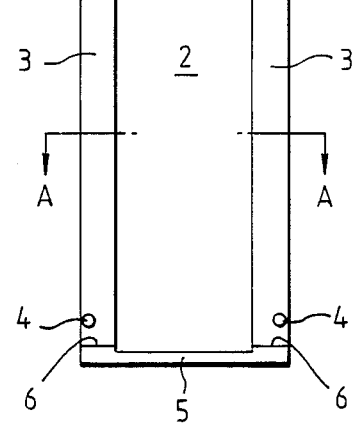
Figure 9:
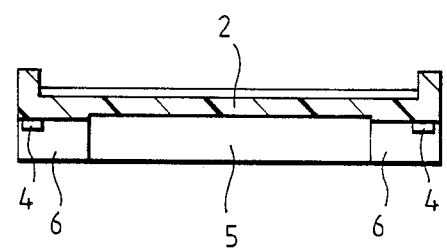

In both forms of the slide clip, the upper end, as seen in FIGS. 2, 4 and 7, includes a funnel-defining element 7.

FIG. 10 illustrates how the slide clip 1 of may be assembled with a microscope slide 10 that is engaged with the flanges 3 and fits between the lugs and/or pegs 4 so that over the major portion of the length of the slide 10, the face thereof adjacent to the clip 1 is spaced, therefrom by a clearance or gap 11 of the order of 70 microns thickness. However, at one end of the slide—the upper end as seen in the drawings—the slide co-operates with the funnel-defining element 7 of the clip to define a flared header 12 communicating with the upper end or inlet 13 of the gap 11. In the case of a slide clip of the form shown in FIGS. 1 to 5, as particularly shown in FIG. 10, the lower end of the clip 1, the corresponding end of the gap 11 constituting an outlet 14 of the latter. In the case of the slide clip of FIGS. 6 to 9, the lower end of the slide 10 engages the shoulders 6 so that a gap of about 0.5 mm is defined between the lug 5 and the majority of the lower end edge of the slide 10.

As noted, the slide clip is intended for co-operation with a support of the form illustrated in FIGS. 11 and 12. This support comprises a generally horizontal rail 20 formed with pairs of parallel laterally projecting fins 21 arranged at an angle of about 70° to horizontal and spaced apart by a distance corresponding to the thickness of the assembly shown in FIG. 10. FIG. 11 shows four such assemblies disposed between five consecutive fins 21.

FIG. 13 is a pictorial representation of the operation of an assembly of slide clip and material carrier (microscope slide) 10 in accordance with the invention, to bring a sequence of liquids into contact successively with material—such as a thin tissue section—carried by the slide so as to be positioned within the gap 11 between the slide 10 and the face of the web 2 of the slide clip. The assembly illustrated includes a slide clip of the form shown in FIGS. 1 to 5 and for reprentational purposes the assembly is shown isolated in space with its header 12 positioned under a dispensing nozzle 25 for liquid to be introduced into the header 12 and thence into the gap 11 to be retained therein by capillary (surface tension) effects, until displaced. The sequence illustrations, below the representation of the assembly, show from left to right, an assembly with the gap 11 filled with a first liquid 26 and the progressive displacement of that liquid by a second liquid 27 introduced into the header 12, the boundary between the two liquids being shown at 28. The first liquid 26 is shown as being discharged from the gap 11 as drops 29 falling from the lower end of the slide 10.

FIG. 14 corresponds with FIG. 13 but illustrates the use of the slide clip of FIGS. 6 to 9. As shown, the lug 5 defines a sump in conjunction with the lower edge of the slide 10 which discharging liquid passes, some being held in the sump by capillary (surface tension) effect. This retained liquid is for instance, available to be drawn up into the gap 11 to replace any loss by evaporation when operating with particularly volatile liquids and/or at elevated temperature. Moreover, liquid held in the sump will also seal the lower end of the gap 11 against ingress of air that might promote unwanted evaporation of liquid in the gap under some operating condition.

Figure 15:
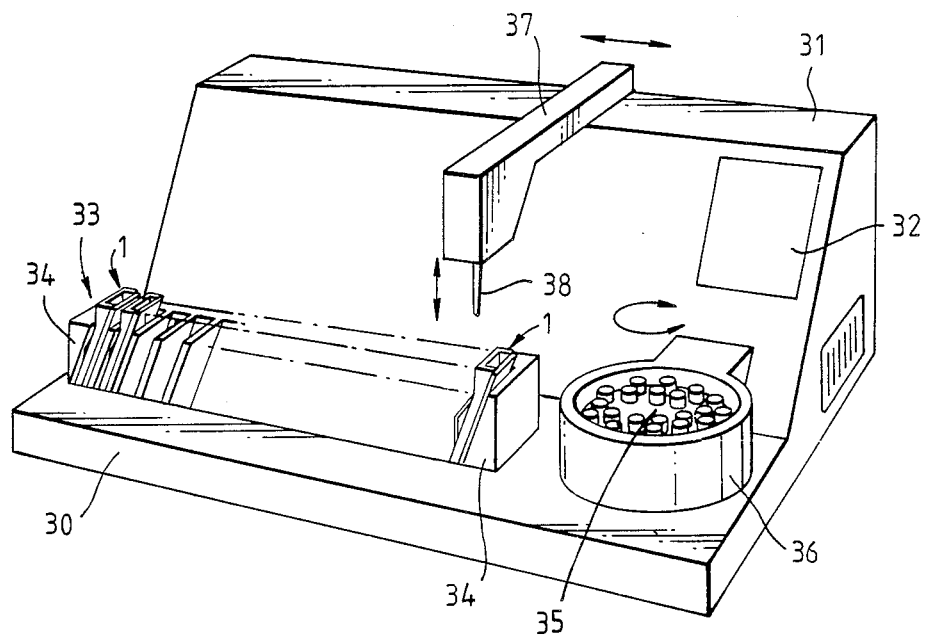
FIG. 15 is an illustration of a machine for performing the method of this invention.

FIG. 15 illustrates the principles of a machine for performing, e.g., an immunostaining routine upon thin section tissue samples on a set of slides 10 assembled with clips 1 in the manner described and supported in a holder comprising a carrier as described with reference to FIGS. 11 and 12.

Thus FIG. 15 shows a machine having a base plate 30 and an upright rear housing 31 for control and drive mechanisms and carrying a control panel diagrammed at 32.

The base plate 30 carries a support 33 of the form described with reference to FIGS. 11 and 12, the rail 20 of that support being suitably carried by end plates 34 that locate in recesses or the like in the base plate 30 for accurated positioning of the support relatively to the latter. In this embodiment the support 33 is adapted to support a total of twenty slide and clip assemblies and has heating coils (not shown) embedded in the faces of its fins 21 for controlled temperature heating of the slides 10 during processing.

The base plate 30 further supports a reagent carousel 35. The reagent carousel supports reagent vials and is indexable to bring a selected vial into a loading position.

The machine further comprises a dispensing head 37 translatable along the length of the machine over the support 33 and equipped with an autopipette 38 and also a dispenser nozzle (not shown) for large volume reagent such as buffer solution. The dispenser nozzle is fed, for instance, by a peristaltic pump (not shown) connected to a liquid reservoir or set of reservoirs via appropriate valves.

In operation of the machine shown in FIG. 15, liquids are dispensed into the headers 12 of the various slide and clip assemblies in the support 33 by suitable positioning of the dispensing head 37 and operation of the autopipette 38 and the dispensing nozzle. The autopipette 38 is employed for transferring reagents from the vials of the carousel 35 to the headers 12, the autopipette 38 picking up a selected reagent following indexing of the vial of that reagent to a pickup position with which that vial may co-operate with the autopipette.

The capillary dimensions of the gap 11 ensure that a very small volume of reagent dispensed into the header 12 from the autopipette 38 passes through the inlet 13 into the gap 11 where it is retained by surface tension effect as a uniform filling of the gap and, thus, layer over the tissue section on the slide 10 within the gap 11. However when another fluid—small volume of reagent from the autopipette 38 or a large volume of buffer solution dispensed by the dispensing nozzle enters the header 12, any liquid held within the gap 11 is displaced, with negligible mixing, to the outlet 14 and thence to a suitable sump in the base plate 30, in the manner described and illustrated in FIGS. 13 and 14.

Thus the machine illustrated in FIG. 15 provides for highly automated performance of tedious and time-consuming processing routines such as immuno-staining with the use of minimum quantities of reagents and can provide for conducting all or part of a routine with the slide carrying a material sample held at a chosen temperature.

However, slide clips embodying the invention may of course be utilised to perform the method manually, a suitable support—preferably of the configuration described with reference to FIGS. 11 and 12—being provided to hold one or more assemblies of slide clip and microscope slide in a convenient attitude for manual introduction of liquids into the header(s) 12 in accordance with a desired routine. To facilitate such manual performance of the method, a suitable support structure may, for instance, be provided within a lidded container that constitutes an enclosure for the assemblies while material samples therein are undergoing contact with liquid, and prevents unwanted evaporation of liquids in use, and contamination of and/or by the ambient atmosphere.

We claim:

1. Apparatus for applying liquids to material on a flat face of a carrier, comprising
   a member including a web having a flat face, flanges projecting from each side of the face of the web to form a channel therebetween, and a cross piece connecting the flanges at one end of the channel, and
   means for locating the carrier on the flanges to form a clearance between the flat face of the web and the face of the carrier which is of capillary dimensions,
   said clearance having an outlet between the lower edge of the carrier and the cross piece and an inlet between the upper edge of the carrier and the face of the web whereby liquid introduced through the inlet and into the clearance will be retained by surface tension until displaced by additional liquid supplied to the inlet.

2. Apparatus of the character defined in claim 1, wherein
   the member has means forming a funnel leading to the inlet.

3. Apparatus of the character defined in claim 1, wherein
   the flanges have shoulders which are spaced above the upper edge of the cross piece to form the clearance at the outlet.

4. Apparatus of the character defined in claim 3, including
   means extending from the cross piece in a direction away from the face of the web to form a sump at the outlet.

* * * * *